United States Patent [19]
Woehrle

[11] Patent Number: 5,846,190
[45] Date of Patent: Dec. 8, 1998

[54] METHOD OF AND APPARATUS FOR RECOGNIZING FALSIFIED PULSE OXIMETRY MEASUREMENTS

[75] Inventor: Dieter Woehrle, Waiblingen, Germany

[73] Assignee: Hewlett-Packard Company, Palo Alto, Calif.

[21] Appl. No.: 728,806

[22] Filed: Oct. 10, 1996

[30] Foreign Application Priority Data

Oct. 10, 1995 [DE] Germany ................. 195 37 646.3

[51] Int. Cl.⁶ .................................................. A61B 5/00
[52] U.S. Cl. ................................. 600/330; 600/336
[58] Field of Search ................... 600/310, 322, 600/323, 330, 473, 476, 336; 356/41

[56] References Cited

U.S. PATENT DOCUMENTS

| | | |
|---|---|---|
| 5,058,588 | 10/1991 | Kaestle . |
| 5,351,685 | 10/1994 | Potratz . |
| 5,368,224 | 11/1994 | Richardson et al. . |
| 5,448,991 | 9/1995 | Polson et al. . |
| 5,503,148 | 4/1996 | Pologe et al. ............ 128/633 |
| 5,570,694 | 11/1996 | Rometsch . |

FOREIGN PATENT DOCUMENTS

| | | |
|---|---|---|
| 0 102 816 | 8/1983 | European Pat. Off. . |
| 0 262 778 | 8/1987 | European Pat. Off. . |
| 37 03 458 | 8/1991 | Germany . |
| 39 38 759 | 11/1991 | Germany . |

OTHER PUBLICATIONS

Von K. Forstner, Pulsoximetrie (Teil 2)[1], Medizintechnik 110. Jg Jun. 1990, pp. 213–217.

Primary Examiner—Jennifer Bahr
Assistant Examiner—Eric F. Winakur

[57] ABSTRACT

A pulse oximeter has several processing channels for measurement signals which are measured during the switched-on phase of transmission diodes and which are used to determine the oxygen saturation ($SpO_2$) of a patient. An additional measurement channel processes an ambient light signal which was measured while the transmission diodes were switched off or their intensity modified, in the same way and thus provides a measure of the spectral composition of the ambient light interference. A useful-to-noise-signal ratio (NSV) is derived from the ambient light signal and a measurement signal, which represents a measure of the signal quality and which can be compared with threshold values (G), where an alarm is triggered if the value falls below the threshold values.

36 Claims, 2 Drawing Sheets

METHOD OF AND APPARATUS FOR RECOGNIZING FALSIFIED PULSE OXIMETRY MEASUREMENTS

FIELD OF THE INVENTION

The present invention relates to the measurement of the oxygen saturation of a patient by pulse oximetry. More particularly, it is concerned with the recognition and display of pulse oximeter measurements which have been falsified by ambient light.

BACKGROUND OF THE INVENTION

Pulse oximetry is a non-invasive technique for monitoring the condition of a patient, for example in an operating theater or in an intensive care unit. For this purpose a sensor or transducer, for example a finger sensor, in which light sources such as light-emitting diodes (LEDs) are integrated, is usually employed. Two or more of these LEDs with different wavelengths (e.g. in the red and infrared band) can be used. The light emitted by these sources is introduced into the tissue of the patient being monitored, and photoreceptors such as photodiodes or phototransistors measure the intensity of the light which has passed through or has been reflected by the tissue. For measuring the transmission, i.e. measuring the light which has passed through the tissue, the transmission and receiver diodes are arranged on different sides of the human tissue, whereas for reflection measurement they are located at the same side of the tissue.

If measurements are taken at two wavelengths at least, the intensity measured on the receiver side can be used to calculate the oxygen saturation in the arterial blood of a patient. A very good summary of the underlying theory, which utilizes the Lambert-Beer law of light absorption, is found in EP 262 778 A. The sensor, which is connected to the pulse oximeter via a detachable transducer cable, usually contains at least two LEDs, which may for example emit light with wavelengths of 650 nm (red) and 1 000 nm (infrared). By altering the field current in the transmission diodes, the intensity of the emitted light can be modified. The photocurrent received by the photoreceptor is measured by the pulse oximeter and used to calculate the oxygen saturation of the arterial blood.

However, a general problem with pulse oximetric measurements is that it is an optical measurement technique which reacts to environmental influences. In other words, ambient light can fall on the photoreceptor of the sensor and accordingly falsify the measurements. Indeed, this effect occurs particularly in clinics, since a large number of optical confusing sources are present there, such as neon tubes, which moreover are operated at different supply frequencies on different continents.

In the past, solutions to exclude this undesired ambient light effect have been sought. One well-known measure, for instance, consists in registering the photocurrent of the photoreceptor with the transmission diode switched off in order to obtain an indicator for the ambient light levels. Thus, the transmission diodes operated in time-division multiplex are switched off periodically, and the signal measured in these so-called dark phases is later deducted from the actual measurements.

However, this dark value measurement, as described in EP 102 816 A2, does not always provide satisfactory results. In particular it has emerged that it only functions satisfactorily when the ambient light interference is of a very low frequency in relation to the repetition rate of the measurement cycles, since the dark value and the measurement signals can never be recorded simultaneously. Since the use of the fluorescent lighting common in many clinics means that up to about 5 kHz spectral components with a disturbing amplitude are still present in the ambient light, during the subsequent sampling of the analog signal the spectral components in the frequency bands surrounding multiples of the sampling rate are convoluted into the useful frequency range and can no longer be eliminated by filtering.

Another method for reducing the influence of ambient light consists in a suitable selection of the repetition rate of the measurement cycles and the arrangement of the measurement and dark phases within a measurement cycle. But this method, too, has its limitations, since for devices operated internationally, supply frequencies both of 50 Hz and of 60 Hz must be taken into account, and since the supply frequencies themselves are also subject to some tolerance.

Still another method for suppressing the disturbing ambient light components is described in U.S. Pat. No. 5,368,224. There, the device switches back and forth between different demultiplexer frequencies, wherein the criterium for selecting a particular demultiplexer frequency is a low noise level in relation to the other frequencies. This method, too, utilizes the selection of a suitable frequency and is subject to the same limitations with respect to the convolution from the harmonic wave ranges into the useful frequency band, as the selection of a suitable excitation repetition rate.

Although all these known solutions improve the signal quality, they cannot completely eliminate the problem of ambient light. Given precisely those often very high light intensities present in a hospital the measurement signal can still experience disturbance despite very good ambient light suppression. There is especially a danger that the sensor is no longer attached properly to the patient or even falls off, so that it is, in effect, only measuring ambient light components. In this case it may happen—and the applicant has in fact heard of such cases—that the sensor and the algorithm behind it believes it recognizes a remnant of a patient signal in the ambient light, i.e. it determines an oxygen saturation value which lies within the alarm limits set at the pulse oximeter. This clearly poses a direct threat to the patient, because the user or operator cannot tell that a mistake has occurred if he or she is not directly beside the patient or the pulse oximeter. Thus, the patient is no longer being monitored, and a critical physiological condition can no longer be reported back to the monitoring person, e.g. the doctor.

Accordingly, it is the object of the instant invention to develop an improved method and a corresponding pulse oximeter which recognizes ambient light. In particular, the aim is to recognize ambient light disturbance which, despite the known measures for suppressing ambient light, still remains in the measurement signal, to determine it in quantitative terms and to derive therefrom an indicator for the quality of the measurement signal which is either reported directly to the user or which triggers an alarm or an "INOP" message when the values fall below or exceed certain limits.

It is a further object of the invention to make use, as far as possible, of components already present in customary pulse oximeters (both hardware and software components) so that as few modifications as possible are required.

BRIEF DESCRIPTION OF THE INVENTION

The invention relates primarily to a method for recognizing falsified pulse oximetry measurements, in which light of at least two different wavelengths is irradiated alternately into the tissue of a patient and by means of at least one photoreceptor the transmitted or reflected light is measured, filtered, converted by analog-digital conversion, and finally analyzed to determined the oxygen saturation in the patient's blood, this method comprising the following steps:

the intensity of at least one excitation light source is modified during repeated time intervals, during these repeated time intervals the photoreceptor measures a modified signal which in comparison to the signal measured with an unmodified excitation light source(s), exhibits a modified useful signal component but a constant ambient light component, the modified signal is filtered and converted by A/D conversion in essentially the same way as the signal measured with an unmodified excitation light source(s), a value representative of the amplitude of the ambient light component is derived from the modified signal after digitization, and the value representative of the amplitude of the ambient light component, or a quantity derived from it, is used as a measure of the signal quality.

The method of the invention is based on the approach of determining by a measurement technique the spectral components in the disturbing frequency bands (and thus goes much further than the subtraction of measured ambient light, the so-called "dark value subtraction" already mentioned). In one embodiment of the method of the invention the ambient light is measured in an additional time interval and its spectral components in the disturbing frequency regions examined. During the ambient light measurement phase, as for the determination of the dark value, the transmitters (e.g. 2 LEDs) are either switched off or their intensity is modified, but the ambient light measurement is not used for deducting the dark value but processed in precisely the same way as the actual measurement signals, i.e. in particular it is filtered and if necessary converted by A/D-conversion. By this means, all spectral components of the ambient light which convolute into the useful frequency band in the measurement channels will also convolute into the region of the useful frequency band in the ambient light channel.

A value representative of its amplitude is now calculated from the digitized ambient light signal. Preferably, this value is the effective value or the peak amplitude of the ambient light signal, or the mean of the rectified ambient light signal. In the same way a value representative of the amplitude of the digitized measurements is derived, i.e. preferably the effective value or the amplitude of the measurement signal, or the mean of the rectified measurement signal. For this second calculation any measurement channel can be used; in the embodiment example this is the infrared measurement channel, but of course it might also be the red one, or both.

The relationship between the two values representative of the amplitude of the measurement signal and of the ambient light signal can now be determined—in one embodiment of the invention—and this relationship can be used as a measure of the signal quality. The relationship can be calculated directly as a quotient and is then to be interpreted as a useful-to-noise-signal ratio. Alternatively, its logarithmic form can also be utilized as a signal-to-noise ratio. This measure of signal quality can now be reported to the user, for instance in a direct numerical or graphical form. For a sensor which has fallen off (and is now only measuring ambient light components) the useful-to-noise-signal ratio is therefore 1, and the signal-to-noise ratio is 0. But it is also possible—and often desirable—to compare the useful-to-noise-signal ratio or the signal-to-noise ratio with a predetermined fixed or variable threshold and if it falls below this threshold to trigger an alarm which draws the user's attention to the fact that there are no longer any valid oxygen saturation measurements available and that the patient is no longer being monitored in this respect. Depending on what is required, the alarm, preferably a so-called "INOP" alarm, can take the form of an acoustic and/or visual signal, can be triggered via an alarm signal to a central unit, etc.

At this point two cases must be distinguished, of which one represents a special case of the other. The special case should be discussed first. This is present if during the time interval during which the modified signal is measured, the excitation light source(s) is/are switched off. Here, the useful-to-noise-signal ratio $NSV_n$ for the measurement phase n can expediently be calculated according to the following formula:

$$NSV_n = \frac{N_n}{U} = \frac{N_n + U}{U} - 1 = \frac{M_n}{U} - 1 \qquad (1)$$

where $M_n$ is the effective value (or the mean, or the peak amplitude) of a measurement signal from measurement phase n, $N_n$ is the effective value (or the mean, or the peak amplitude) of the useful signal from measurement phase n, and U is the effective value (or the mean, or the peak amplitude) of the ambient light signal with the excitation light source switched off. Naturally, instead of the useful-to-noise-signal ratio, the signal-to-noise ratio ($20 \cdot \log NSV_n$) can also be employed.

The generalization of the case just described is obtained if the excitation light source(s) is/are not switched off during the time interval in which the modified signal is measured, but intensity-modified instead. In this case the modified signal contains both measurement and ambient light components. But in this case, too, a representative value can be calculated for the pure ambient light signal, or the useful-to-noise-signal ratio can be determined, as the following consideration shows:

Let $M_{n,1}$ be the effective value or the amplitude of the alternating signal component in measurement phase n with intensity 1, and $M_{m,2}$ be the corresponding value in measurement phase m with the (modified) intensity 2 (n=m is possible). Let $N_{n,1}$ be the effective value or the amplitude of the alternating signal component of the useful signal in measurement phase n with intensity 1, and let U be the effective value or the amplitude of the ambient light signal (=noise signal). Then $$M_{n,1} = N_{n,1} + U \qquad (2a)$$

$$M_{m,2} = a \cdot N_{n,1} + U \qquad (2b)$$

Factor a, by which the useful signal changes with modulated excitation light source intensity, is assumed to be known. It can either be derived from the sensor characteristic or calculated from the following formula:

$$a = \frac{G_{m,2}}{G_{n,1}} \qquad (3)$$

(where $G_{n,1}$=direct signal component of the measurement signal in measurement phase n with intensity 1 and $G_{m,2}$= direct signal component of the measurement signal in measurement phase m with intensity 2).

Substituting the two formulas (2a) and (2b) gives $$U = \frac{M_{m,2} - a \cdot M_{n,1}}{(1-a)} \quad (4)$$

for the pure ambient light component and the useful-to-noise-signal ratio $$NSV_{n,1} = \frac{M_{n,1} \cdot (1-a)}{M_{m,2} - a \cdot M_{n,1}} \quad (5)$$

($NSV_{n,1}$=useful-to-noise-signal ratio for measurement phase n with intensity 1)
and the signal-to-noise ratio $$SNR_{n,1} = 20 \cdot \log NSV_{n,1} \quad (6)$$

($SNR_{n,1}$=signal-to-noise ratio for measurement phase n with intensity 1)
As is clearly apparent, the above formula (5) can be simplified to formula (1) if intensity 2 is set to zero ($G_{m,2}$=0), since in that case a=0. The definition of the signal-to-noise ratio, too, is reduced to the first case again.

The method of the invention provides an indicator for the signal quality (or, reciprocally, for the strength of the interfering ambient light signal), which offers additional security against incorrect measurements. Thus it can be detected with certainty whether the sensor is (still) attached to the patient properly. In particular, an alarm is certain to be triggered if the sensor has fallen off the patient. (Without the method of the invention for recognizing falsified measurements there is a danger that the ambient light signal is misinterpreted as the patient signal and no alarm is triggered). But even when the sensor is attached to the patient correctly, the method of the invention offers additional security against threshold alarms not being triggered, e.g. when a patient displays an $SpO_2$ measurement below the threshold set by the doctor, but due to environmental influences a value above this threshold is measured and displayed. Furthermore, if the useful-to-noise-signal ratio and/or the signal-to-noise ratio is displayed either in numerical or graphical form, this allows the user to improve the quality of the measurement, e.g. by changing the way the sensor is applied, covering up the sensor location (screening from ambient light), etc.

The useful signal and the noise signal ratios are not the only quantities which can be representative of the amplitude of the ambient light component and thus serve as a measure of the signal quality. Alternatively it is also possible to use other quantities for this purpose, particularly the amplitude of the ambient light component itself or the difference between the amplitude of the ambient light component and the amplitude of a value representative of the digitized measurement signal.

It is readily appreciated that the method of the invention is preferably employed in conjunction with other measures for suppressing ambient light. Although it is possible in principle to employ only the method of the invention, better results are generally expected if the method is combined with other known measures. One option is the combination with dark value subtraction, in which the ambient light component is measured and deducted both from the measurement signals and the ambient light signal obtained according to the invention. This increases the security against false measurements.

If an additional channel is used to obtain a measurement for altered intensity, it is guaranteed that by the identical or quasi-identical signal processing of the measurement signals, all disturbances which overlay the measurement signal in the useful channels are also made visible in the additional channel. For this purpose an attempt is made to sample the measurement signals and the signal in the additional channel with the same sampling rate, to conduct the same dark value deduction for all these signals, to subject them to the same filtering, etc. In particular, both signal groups are subjected to a low pass or a bandpass filtering; preferably also the same high pass filtering and rectification. By means of the high pass filtering only the alternating components of the measurement and ambient light signals are used in calculating the ratio of the values representative of the amplitudes of these signals. Rectification and low pass filtering allow a mean value for the signal in question to be formed which is especially suitable for determining the useful-to-noise-signal ratio and the signal-to-noise ratio derived therefrom.

It is also advantageous for the ambient light phase to come directly before or after the dark value phase in the measurement method operated in time-division multiplex. This guarantees that the ambient light signal is only eliminated completely by dark value subtraction for frequencies at which the ambient light disturbances in all measurement channels also cancel each other out completely.

A particular advantage of the method of the invention is the fact that only relatively slight modifications of existing pulse oximeters are required for its implementation. In the following, two preferred embodiments of the invention are introduced which do not require any (or at any rate require only very few) circuit modifications, but merely require essentially an adaptation of the programming.

According to a first embodiment the output signal of the photoreceptor is applied to a multiplexer and each measurement signal is distributed between at least one processing channel, where a separate processing channel, which is essentially identical to the processing channels allocated to the measurement signals, is provided for the ambient light signal. This solution is above all the obvious choice for pulse oximeters which already possess a redundant processing channel (which is often the case), and whose time-division multiplex scheme permits the operation of this additional processing channel.

However, if this solution is not possible or desired, the processing of the ambient light signal can also take place in one of the measurement channels already available. For this purpose it is expedient to switch off the intensity of the excitation light source periodically and to utilized the resulting interruption to record and process ambient light signals. Since the oxygen saturation is a relatively slow-changing patient parameter, a short-term interruption is not of very great consequence, and so this may represent an attractive solution. According to the generalization discussed above, it is possible only to modify the intensity of one excitation light source (i.e. the measurement signal is not switched off, but only its intensity modified), and thus an interruption of oxygen saturation measurement can be avoided completely.

The invention also relates to a pulse oximeter for measuring the oxygen saturation of a patient with
- at least one excitation light source which irradiates light of at least two wavelengths into the tissue of the patient;
- at least one photoreceptor which measures the light which has passed through or been reflected by the tissue;
- measurement signal channels for the measurement signals received by the photoreceptor, where each measurement signal processing channel comprises filters and analog-digital converters for filtering and analog-digital conversion of these measurement signals;
- a processing unit, preferably a microprocessor, which calculates the oxygen saturation from the measurement signals which have been filtered and converted by analog-digital conversion; with an ambient light processing channel comprising filters and possibly analog-digital converters in the same manner as the measurement signal processing channels, but where the ambient light processing channel is only activated in time intervals in which the excitation light source(s) is/are switched off and/or modulated.

BRIEF DESCRIPTION OF THE FIGURES

The invention will now be explained in more detail using a preferred embodiment with reference to the accompanying figures, which depict the following.

DETAILED DESCRIPTION OF PREFERRED EMBODIMENTS

Figure 1:
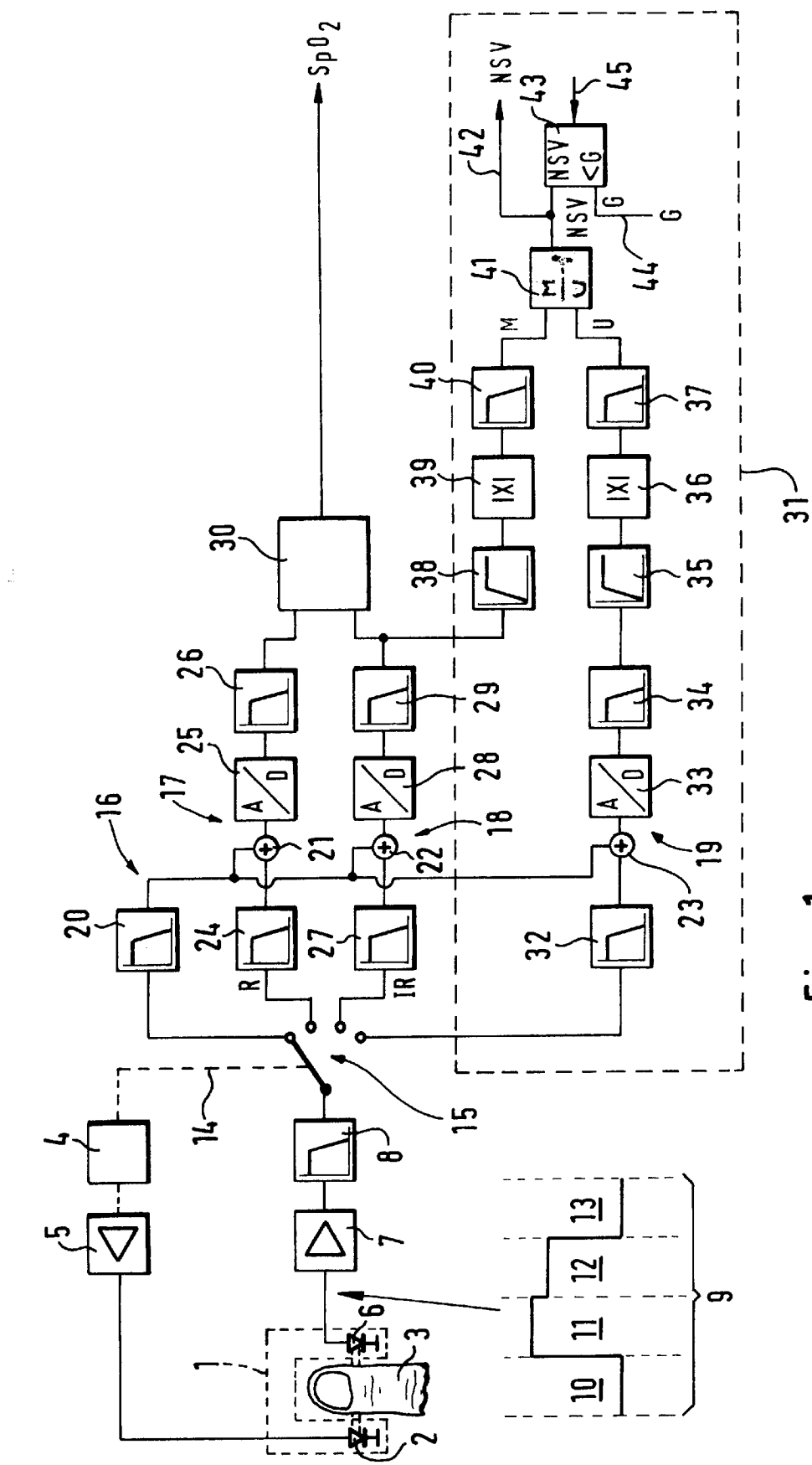
FIG. 1 a block diagram of a first embodiment of the invention.

FIG. 1 shows the circuitry of a pulse oximeter including the accompanying sensor, in the form of a block diagram. The sensor is represented schematically as 1 (broken line) and in reality it may for example be a finger sensor as described in DE-C-3 703 458. It comprises a transmission diode 2, also represented schematically, which transmits light into the finger 3 of a patient. To conduct pulse oximetry measurements it is necessary to subject tissue to light of at least 2 different wavelengths. Transmission diode 2 can thus in practice consist of two light-emitting diodes in antiparallel arrangement, as described in U.S. Pat. No. 5,058,588, for example. In this embodiment one transmission diode is operated by pulses of one polarity, while the other transmission diode is operated by pulses of the opposite polarity. In practice, a red and an infrared light-emitting diode are generally employed.

A time-control unit 4 controls when which of the transmission diodes is active. This time-control unit is connected to the transmission diode via an amplifier circuit 5. In practice this connection is made by the sensor cable, i.e. amplifier circuit 5 is still a component of the pulse oximeter, whereas transmission diode 2 is integrated into the sensor.

A photodiode 6 which is also part of sensor 1, receives the light of transmission diode(s) 2 which is transmitted through finger 3. The intensity of the light received is attenuated by absorption in the tissue of finger 3, and the oxygen saturation in the patient's blood can be determined from the attenuation using known methods.

Control of transmission diodes 2 by time control unit 4 is performed with the time division multiplex method. In the embodiment example illustrated there are 4 regularly recurring time intervals. During the first time interval the transmission diodes are switched off, and the ambient light component (here, also known as "dark value") is measured. During the second time interval the red transmission LED is switched on and during the third time interval the infrared transmission LED is switched on. The fourth time interval is intended for measuring the ambient light signal in a manner to be described later, and following on from this, for calculating the useful-to-noise-signal ratio.

The signal received by photodiode 6 is first applied to an input amplifier 7 and from there applied to an input filter 8 with low pass characteristic. Since in time division multiplex the transmission and thus also the received signal is represented as a sequence of pulses with higher-frequency components, a relatively high threshold frequency must be selected for input filter 8. In this way the measurements can settle at their final value with sufficient accuracy within the separate measurement phases.

The signal on the line between photodiode 6 and input amplifier 7 (in practice the sensor cable) is represented once again in detail in subfigure 9. During a first phase 10 the dark value is measured, during a second phase 11 the red value, during a third phase 12 the infrared value and during a fourth phase 13 the ambient light signal is measured. The whole signal pattern is then repeated continually while the measurement is in progress.

As depicted by the dotted line 14, time-control unit 4 also controls a multiplexer 15 synchronously with the excitation signals. The received signal is then distributed between a total of four processing channels labeled by reference symbols 16 to 19. Each of these channels is responsible for processing a measurement signal, the dark value or the ambient light signal.

Processing channel 16 is responsible for processing the dark value, i.e. the signal recorded during time interval 10 (see time diagram 9) is processed there. This processing channel consists essentially of a low pass filter 20 which band-limits the signal and serves as hold circuit for each measurement. As low pass filter 20 no longer has to be able to follow the combined pulse sequence represented in time diagram 9, but only the frequency of the dark value signals, its threshold frequency can be selected far lower than the threshold frequency of input filter 8. The output signal of low pass filter 20 is then relayed to the three summing points 21, 22 and 23, whose function will be described in more detail in the following.

Processing channel 17 functions for the measurement signal of the red LED in a similar fashion to dark value processing channel 16. This channel is only active, i.e. selected by multiplexer 15, when the red transmission diode is switched on (compare reference symbol 11 in time diagram 9). The signal transmitted through finger 3 of the patient during the period in which the red LED is switched on is applied to a low pass filter 24, which has a similar or the same characteristic as low pass filter 20. Next, the output signal of low pass filter 24 is applied to summing point 21; there, the dark value, i.e. the ambient light component of the light received by photodiode 6, is deducted. The resulting signal then arrives at an analog-digital converter 25 and after digitization is band-limited again in digital low pass 26.

The infrared processing channel 18 with low pass filter 27, summing point 22, analog-digital converter 28 and digital low pass 29 functions in corresponding manner, except that here the infrared received signals 12 are taken into account. The output signals of the two digital low passes 26 and 29 are now applied to a processing unit 30—typically a microprocessor, which calculates on the basis of the known algorithm the value for the patient's oxygen saturation from these values (referred to as $SpO_2$ in FIG. 1).

The components of the pulse oximeter described so far correspond to the state of the art. A novelty, on the other hand, are the components shown in dashed block 31, with which a measure of the quality of the oxygen saturation signal and in particular its falsification by ambient light components may be calculated and possibly used to reject the $SpO_2$ measurements or to alert the user.

While processing channel 19 is active, transmission diodes 2 are also switched off, see reference symbol 13. Processing of the ambient light signal in channel 19 takes place in the same manner as the processing of the red and the infrared signals in channels 17 and 18. That means that the signal measured by photodiode 6 is first band-limited in low pass 32; the dark value is deducted from the output signal of this low pass (summing point 23); the deducted signal is digitized in analog-digital converter 33 and band-limited again in digital low pass 34. Thus far, the processing of the ambient light component corresponds to the processing of the red and the infrared measurements in components 21, 22 and 24 to 29.

The ambient light signal at the output of digital low pass 34 is further applied to a high pass 35 which selects the alternating component of the ambient light signal. There follows rectification by rectifier 36 and averaging by low pass filter 37. At the output of low pass filter 37 an essentially time-constant signal is now present, which is proportional to the amplitude of the ambient light signal.

In a further processing path consisting of components 38 to 40, the infrared measurement signal is processed in the same way as occurs in components 35 to 37 for the ambient light signal. Here it must be emphasized that the signal processed by components 38 to 40 must be a measurement signal, i.e. a signal which was recorded with the transmission diode switched on; but the infrared channel must not necessarily be selected, the red measurement channel may also be connected instead.

By means of processing in high pass filter 38, rectifier 39 and low pass filter 40 a rectified signal is produced at the output of the latter which is proportional to the amplitude of the infrared measurement signal. Now the output of low pass filters 37 and 40 is applied to computation or ratio-calculation unit 41, which calculates the useful-to-noise-signal ratio. Here, M is the value proportional to the amplitude of the infrared measurement signal, but U is the value proportional to the amplitude of the ambient light signal. The useful-to-noise-signal ratio is calculated according to the following formula $$NSV_n = \frac{M_n}{U} - 1 \quad (7)$$

where $M_n$ is the value proportional to the amplitude of the signal from measurement phase n, U the value proportional to the amplitude of the ambient light signal, and $NSV_n$ the useful-to-noise-signal ratio from measurement phase n.

Of course, instead of the useful-to-noise-signal ratio it is also possible to calculate the signal-to-noise ratio. This is obtained from the following formula $$SNR_n = 20 \cdot \log NSV_n \quad (8)$$

where $SNR_n$ is the signal-to-noise ratio corresponding to measurement phase n.

It is of course equally possible to use the peak amplitude or the effective value of the rectified ambient light signal, instead of its mean value.

The useful-to-noise-signal ratio can now be processed further algorithmically, as indicated by line 42. A typical implementation is illustrated in even more detail in FIG. 1. Here, the calculated value of the useful-to-noise-signal ratio NSV is applied to a comparator 43 which compares this value with a threshold value G (line 44). If the useful-to-noise-signal ratio is less than this threshold, i.e. if the useful signal is too small in comparison to the disturbing ambient light signal and is overlaid by it to a large degree, an alarm can be generated via line 45, e.g. a visual and/or acoustic alarm to summon a human operator to the bed of the patient being monitored. This case may arise in particular if the sensor has fallen off the patient, but, due to strong ambient light disturbances, a fictitious $SpO_2$ value, which lies within the alarm limits set for this measurement, is measured. In this case, too, the mimic according to the present invention can detect that the useful-to-noise-signal ratio has become too small, and then generates either an ambient light or noise signal alarm via line 45. It is of course also possible simply to reject the corresponding measurements rather that generate an alarm.

It is readily appreciated that instead of the useful-to-noise-signal ratio the signal-to-noise ratio can be used to trigger an alarm. If the sensor has fallen off, the useful-to-noise-signal ratio will be 1 and the signal-to-noise ratio will be 0.

In consequence of the fact that the procedure for processing the ambient light in processing channel 19 is identical to that for processing the measurement signals in measurement channels 17 and 18, the spectral components of the ambient light in the disturbing frequency ranges are measured. This means that all spectral components of the ambient light which convolute into the measurement channels in the useful frequency band, also convolute into the ambient light processing channel in the useful frequency band range. Subsequently, the spectral components of the ambient light in the useful frequency band (e.g. 0.5 to 5 Hz) are selected by a bandpass filter, the effective value, the amplitude or the mean value of the rectified signal is determined and its ratio to the effective value, the amplitude or the mean value of the rectified useful signal determined. What is essential here is that the signal processing in the measurement channels and in the ambient light processing channel is identical (i.e. the same sampling rate, the same dark value deduction, the same filtering, etc.), in order to guarantee that all disturbances that overlay the signal in the useful signal or measurement channels is also visible in the ambient light channel.

Finally, the useful-to-noise-signal ratio NSV can be brought directly to the attention of the user, e.g. in numerical or graphical from. The user then has a measure of the signal quality and can attempt to influence this positively, e.g. by altering the application or the arrangement of the sensor, by covering up the sensor location (screening from environmental influences) etc.

It is advantageous to begin the ambient light phase directly before or after the dark phase. This guarantees that the ambient light signal is only eliminated completely by dark value deduction for frequencies at which the ambient light disturbances in all measurement channels also cancel each other out completely. In FIG. 1 this condition is met since directly after the ambient light phase 13 there is another dark phase 10 (time diagram 9 is repeated continually during measurement, as described above).

In the example described here the excitation light sources are switched off periodically in order to determine the useful-to-noise-signal ratio. But of course, as outlined in the introductory description, the same result may be achieved by periodically modulating the excitation light sources.

As an alternative to the embodiment shown in FIG. 1. it is also possible not to use a separate ambient light processing channel (reference symbols 19 in FIG. 1) but to conduct the ambient light measurement in the measurement channels themselves instead. This saves on circuit components; however, if their operation as measurement channels is interrupted for the ambient light measurement, no oxygen saturation measurements can be taken in the measurement channels during the ambient light measurement. Therefore, in the form of time diagrams, FIGS. 2a and 2b show a better solution in which only the intensity of the excitation light sources in the measurement channels is modulated, without reducing the intensity to zero.

Figure 2A:
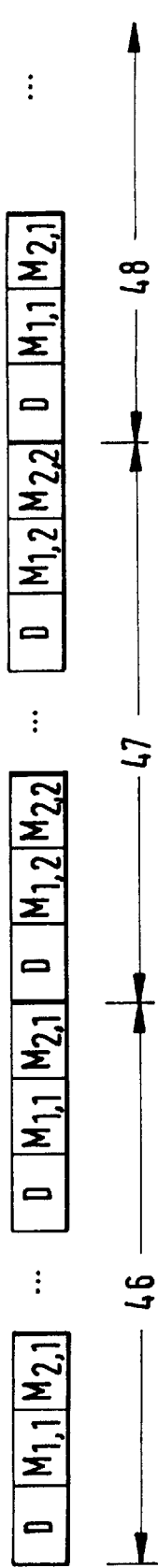
FIG. 2a and 2b time-flow diagrams of alternative embodiments of the invention.
Figure 2B:
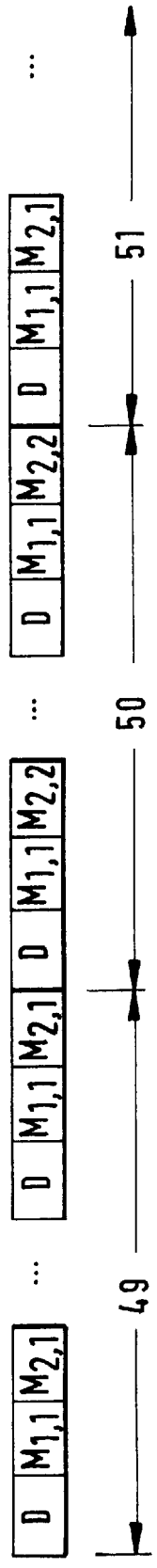

According to FIG. 2a measurement channels 17 and 18 are utilized for the ambient light measurement, this being achieved by intensity modulation of both excitation light sources. In this figure, reference symbol 46 refers to a phase of $SPO_2$ measurement with the excitation light source in normal operation, i.e. without intensity modulation. Three phases which are repeated periodically are the dark phase (D), measurement phase 1 with intensity 1 ($M_{1,1}$) and measurement phase 2 with intensity 1 ($M_{2,1}$).

In time period 47, in contrast, measurements are conducted with modified intensity. This means that measurement signal 1 is measured with intensity 2 ($M_{1,2}$), as is measurement signal 2 ($M_{2,2}$). Here, too, the letter D refers to the dark phase via processing channel 16. During phases $M_{1,2}$ and $M_{2,2}$ therefore, a mixed measurement for the measurement signals and the spectral components of the ambient light is obtained, which is determined in the same way as the actual measurements, since both have been conducted via the same processing channel. In time interval 48, on the other hand, the $SpO_2$ measurement is resumed with the original intensity 1, as can be identified by the repeated sequence $M_{1,1}$ and $M_{2,1}$.

Of course it is also possible to modify the intensity of only one of the excitation light sources. This case is depicted in FIG. 2b. Time periods 49 and 51 are identical to periods 46 and 48 in FIG. 2a; in period 50, however, only measurement phase 2 is set to intensity 2 ($M_{2,2}$), while measurement phase 1 is conducted with the original unmodulated intensity 1 ($M_{1,1}$).

The solution shown in FIGS. 2a and 2b has the decided advantage, that a separate measurement channel for the ambient light signal does not have to be provided. Furthermore, this method can be employed for all types of ambient light suppression.

I claim:

1. Method of detecting falsified pulse oximetry measurements in which light of at least two wavelengths alternately irradiates tissue of a patient and an excitation light source is arranged to cause light transmitted through or reflected from the tissue to be measured with a photoreceptor, filtered, converted via A/D conversion and subsequently analyzed to determine the oxygen saturation in the patient's blood, comprising modifying the intensity of the light of the excitation light source during repeated sequential time intervals, measuring with the photoreceptor the intensity of a modified signal during the repeated time intervals which in comparison to the signal measured with unmodified excitation light source(s) has a modified useful signal component and a constant ambient light component, filtering and converting the modified signal to derive a converted modified signal by A/D-conversion in essentially the same way as the signal measured with an unmodified excitation light source is filtered and converted, deriving from the converted modified signal a value representative of the amplitude of the ambient light component, the value representative of the amplitude of the ambient light component, or a quantity derived from the value, being a measure of the signal quality.

2. Method according to claim 1, further including setting to zero, during repeated time intervals, the intensity of the light emitted by the source.

3. Method according to claim 1, wherein the quantity used as a measure of the signal quality is calculated as a useful-to-noise-signal ratio in which a value representative of the amplitude of a digitized measurement signal is set in relationship to the value representative of the amplitude of the ambient light component, or is calculated as a signal-to-noise ratio in a logarithmic form of the useful-to-noise-signal ratio.

4. Method according to claim 3, wherein the values representative of the amplitudes of the measurement signal or the ambient light component are calculated as effective values or mean values, or as peak amplitudes.

5. Method according to claim 1, wherein the quantity used as a measure of the signal quality is the amplitude of the ambient light component.

6. Method according to claim 1, wherein the quantity used as a measure of the signal quality is the difference between the amplitude of the ambient light component and the amplitude of a value representative of a digitized measurement signal resulting from the A/D conversion.

7. Method according to claim 1, wherein the measure representing signal quality is derived in response to only an alternative component of the ambient light component.

8. Method according to claim 1 further including visually displaying the quantity used as a measure of the signal quality.

9. Method according to claim 1 further including comparing the quantity used as a measure of the signal quality with at least one threshold value, and rejecting the measurement or generating an alarm in response to the quantity used as a measure of the signal quality having a predetermined relation relative to the threshold.

10. Method according to claim 1, further including high pass filtering both the signals measured with an unmodified excitation light source and the signals measured with the modified excitation light.

11. Method according to claim 10, further including rectifying and high pass filtering both the signals measured with the unmodified excitation light source and the modified signals measured with modified excitation light source.

12. Method according to claim 1, further including multiplexing the output signal of the photoreceptor and distributing each measurement at least one processing channel, and supplying the ambient light signal to a separate processing channel, which is essentially identical to the processing channels assigned to the measurement signals.

13. Method according to claim 1 further including periodically interrupting the recording and the processing of measurement signals and recording and processing the resulting interrupted ambient light signals.

14. Method of claim 1, further including recording dark values during a time interval while the excitation light source is switched off and only ambient light is incident on the photoreceptor, and subsequently deducting the dark values from both the measurement signals and the ambient light signal.

15. Method according to claim 14, wherein the time intervals during which the dark values are recorded and during which the ambient light signal is recorded follow each other directly in any order.

16. Pulse oximeter for measuring the oxygen saturation of a patient, comprising at least one excitation light source for irradiating tissue of the patient with light of at least two wavelengths;

at least one photoreceptor for measuring the light from said source as transmitted through or reflected by the tissue;

measurement signal processing channels for the measurement signals received by the photoreceptor, each measurement signal processing channel comprising filters and an analog-digital converter for filtering and A/D-conversion of the measurement signals in substantially the same ways; and a processing unit for calculating the patient oxygen saturation from the measurement signals which have been filtered and converted by A/D-conversion; and an ambient light processing channel including filters and an analog-digital-converter having substantially the same characteristic as the filters and analog-digital-converters of measurement signal processing channels, the ambient light processing channel being only activated during time intervals while the intensity of the excitation light source is switched off or modulated.

17. Pulse oximeter according to claim 16, further including a dark value processing channel activated only during time intervals while the excitation light source is switched off, and circuitry for deducting the dark value from the measurement signals and the ambient light signal.

18. Pulse oximeter for measuring the oxygen saturation of a patient comprising an excitation circuit for at least two excitation wavelengths of differing wavelengths;

a receiver circuit for receiving signals from a photoreceptor;

plural measurement signal processing channels for the measurement signals received by the receiver circuit, each measurement signal processing channel comprising a filter and analog-digital-converter for filtering and A/D-conversion of these measurement signals; and a processing unit for calculating the oxygen saturation from the measurement signals which have been filtered and converted by A/D-conversion; and an ambient light processing channel which is only activated in time intervals while the intensity of the excitation circuit is in a condition causing only background optical energy or modulated optical energy to be incident on the photoreceptor, the ambient processing channel including filters and analog-digital-converters for processing a signal received from the photoreceptor in the same manner as the measurement signal processing channels.

19. Pulse oximeter according to claim 18, wherein the ambient light processing channel processes to derive at least one measurement signal and one ambient light signal, the ambient light processing channel including a computation unit responsive to the at least one measurement signal and one ambient light signal for calculating values representative of the amplitudes of the digitized measurement signal and the digitized ambient light signal and for calculating the ratio between the two.

20. Pulse oximeter according to claim 19, wherein the computation unit comprises at least one rectifier and a high pass filter.

21. Pulse oximeter according to claim 20, characterized in that the computation unit calculates the ratio between the values representative of the amplitudes of the measurement signal and the ambient light signal as a useful-to-noise-signal ratio or in logarithmic form as a signal-to-noise ratio.

22. A method of detecting the relative amounts of signal and noise in pulse oximetry measurements of a patient comprising energizing an optical energy source so tissue of the patient is irradiated by the source with optical energy having a first wavelength, the tissue being irradiated with the first wavelength during repeated sequential first time intervals, the tissue modifying the first wavelength during the first time intervals as a function of oxygen content, detecting in a photodetector the intensity of the first wavelength as modified during the first intervals, detecting the intensity of ambient optical energy incident on the photodetector during repeated sequential second and third differing time intervals when only ambient optical energy is incident on the photodetector, measuring the intensity of the detected optical energy incident on the photodetector during the first, second and third time intervals, deriving a first measure of the relative values of the measured intensities during the first and second intervals, deriving a second measure of the relative values of the measured intensities during the second and third intervals, processing the first measure in a predetermined manner to derive a first signal including noise and information used to determine oxygen saturation of the patient, processing the second measure in the predetermined manner to derive a second signal indicative of noise in the first signal, and comparing the amplitudes of the first and second signals to derive an indication of the relative amounts of signal and noise of the optical energy detected by the photodetector during the first interval.

23. The method of claim 22 wherein the amplitude is detected during the first, second and third intervals by low pass filtering an output signal of the photodetector.

24. The method of claim 23 wherein the first measure is processed by (a) high pass filtering it to derive a first response and (b) determining absolute value of the first response to derive the first signal, and the second measure is processed by (a) high pass filtering it to derive a second response and (b) determining absolute value of the second response to derive the second signal.

25. The method of claim 22 wherein the first measure is processed by (a) high pass filtering it to derive a first response and (b) determining absolute value of the first response to derive the first signal, and the second measure is processed by (a) high pass filtering it to derive a second response and (b) determining absolute value of the second response to derive the second signal.

26. The method of claim 22 wherein the first measure is processed by: (a) analog-to-digital converting it to derive a first digital signal, (b) low pass filtering the first digital signal to derive a second digital signal, (c) high pass filtering the second digital signal to derive a third digital signal, and (d) determining absolute value of the third digital signal to derive the first signal; the second measure being processed by: (a) analog-to-digital converting it to derive a fourth digital signal, (b) low pass filtering the fourth digital signal to derive a fifth digital signal, (c) high pass filtering the fifth digital signal to derive a sixth digital signal, and (d) determining absolute value of the sixth digital signal to derive the second signal.

27. The method of claim 22 in combination with measuring oxygen saturation of the patient by irradiating tissue of the patient with optical energy having a second wavelength during repeated sequential fourth time intervals, the tissue modifying the second wavelength as a function of oxygen content, further comprising detecting in the photodetector the intensity of the second wavelength as modified during the fourth interval, measuring the intensity of the detected optical energy incident on the photodetector during the fourth time interval, deriving a third measure indicative of the relative values of the measured intensities during the second and fourth intervals, processing the third measure in a predetermined manner to derive a third signal including noise and information used to determine oxygen saturation of the patient, combining the first and third signals to derive a measure of the oxygen saturation of the patient.

28. The method of claim 22 further including detecting the ambient optical energy incident on the photodetector by recording the intensity of radiation incident on the photodetector during the second and third intervals when the source is switched off, and comparing the amplitudes of the optical energy incident on the photodetector during the second and third time intervals to provide a measure of ambient optical energy incident on the photodetector.

29. The method of claim 28 wherein the second and third time intervals follow each other directly in any order.

30. The method of claim 28 wherein the measure of ambient optical energy incident on the photodetector is determined by subtracting the compared amplitudes.

31. Apparatus for detecting the relative amounts of signal and noise in a pulse oximetry measurement of a patient comprising an optical energy source for irradiating tissue of the patient with a first wavelength during repeated sequential first time intervals, the tissue modifying the first wavelength during the first time intervals as a function of oxygen content, a photodetector for detecting the intensity of the first wavelength as modified during the first intervals, circuitry for measuring the intensity of ambient optical energy incident on the photodetector during the first time intervals as well as during repeated differing sequential second and third time intervals while the optical energy source is inactive and only ambient optical energy is incident on the photodetector, a detector arrangement responsive to the measuring circuitry for detecting the intensity of the optical energy incident on the photodetector during the first, second and third time intervals, first deriving circuitry responsive to the detector arrangement for deriving a first measure of the relative values of the detected intensities during the first and second intervals, second deriving circuitry responsive to the detector arrangement for deriving a second measure of the relative values of the detected intensities during the second and third intervals, first processing circuitry responsive to the first deriving circuitry for processing the first measure in a predetermined manner to derive a first signal including noise and information used to determine oxygen saturation of the patient, second processing circuitry responsive to the second deriving circuitry for processing the second measure in the predetermined manner to derive a second signal indicative of noise in the first signal, and comparing circuitry for comparing the amplitudes of the first and second signals to derive an indication of the relative amount of signal and noise in the intensity of the first wavelength detected by the photodetector during the first interval.

32. The apparatus of claim 31 further including low pass filter circuitry responsive to an output signal of the photodetector for detecting the amplitude of the incident optical energy during the first, second and third intervals.

33. The apparatus of claim 32 wherein the first deriving circuitry includes (a) a first high pass filter for deriving a first response and (b) absolute value determining circuitry responsive to the first response for deriving the first signal, the second deriving circuitry including a second high pass filter for deriving a second response, and (c) absolute value determining circuitry responsive to the second response for deriving the second signal.

34. The apparatus of claim 31 wherein the first deriving circuitry includes (a) a first high pass filter for deriving a first response, (b) absolute value determining circuitry responsive to the first response to derive the first signal, the second deriving circuitry including a second high pass filter for deriving a second response, and (c) absolute value determining deriving circuitry responsive to the second response for deriving the second signal.

35. The apparatus of claim 31 wherein the first deriving circuitry includes an (a) analog-to-digital converter for converting the first measurement to derive a first digital signal, (b) a low pass filter responsive to the first digital signal for deriving a second digital signal, (c) a high pass filter responsive to the second digital signal for deriving a third digital signal, and (d) absolute value determining circuitry responsive to the third digital signal for deriving the first signal; the second deriving circuitry including: (a) an analog-to-digital converter for converting the second measure for deriving a fourth digital signal, (b) a low pass filter responsive to the fourth digital signal for deriving a fifth digital signal, (c) a high pass filter responsive to the fifth digital signal for deriving a sixth digital signal and (d) absolute value determining circuitry responsive to the sixth digital signal for deriving the second signal.

36. The apparatus of claim 31 wherein the optical source derives a second wavelength during repeated sequential fourth time intervals, the tissue modifying the second wavelength as a function of oxygen content, the photodetector detecting the intensity of the second wavelength as modified during the fourth interval, the detector arrangement detecting the intensity of the optical energy incident on the photodetector during the fourth time interval, third deriving circuitry for deriving a third measure indicative of the relative values of the detected intensities during the second and fourth intervals, processing circuitry for processing the third measure in a predetermined manner for deriving a third signal including noise and information, and combining circuitry responsive to the first and third signals for deriving a measure of oxygen saturation of the patient.

* * * * *